United States Patent [19]

Smullen et al.

[11] Patent Number: 5,540,838
[45] Date of Patent: Jul. 30, 1996

[54] STIMULATION OF MICROBIAL PARA-DECHLORINATION OF POLYCHLORINATED BIPHENYLS

[75] Inventors: Lynn A. Smullen, Amsterdam; Donna L. Bedard, Loudonville, both of N.Y.

[73] Assignee: General Electric Company, Schenectady, N.Y.

[21] Appl. No.: 459,869

[22] Filed: Jun. 2, 1995

[51] Int. Cl.[6] ............................ C12N 1/38; C02F 3/00; B09B 3/00
[52] U.S. Cl. ...................... 210/610; 210/612; 210/614; 210/909; 435/244; 435/262.5
[58] Field of Search ....................... 210/601, 610, 210/611, 612, 614, 909; 435/34, 244, 262, 262.5

[56] References Cited

U.S. PATENT DOCUMENTS

| | | | |
|---|---|---|---|
| 4,477,570 | 10/1984 | Colaruotolo et al. | 435/253 |
| 4,493,895 | 1/1985 | Colaruotolo et al. | 210/601 |
| 4,664,805 | 5/1987 | Focht | 210/611 |
| 4,816,403 | 3/1989 | Roy | 210/909 |
| 4,843,007 | 6/1989 | Bedard et al. | 435/262 |
| 4,843,009 | 6/1989 | Bopp | 435/262 |
| 4,876,201 | 10/1989 | Bedard et al. | 210/601 |
| 5,227,069 | 7/1993 | Van Dort et al. | 210/610 |
| 5,484,729 | 1/1996 | DeWeerd et al. | 210/610 |

OTHER PUBLICATIONS

"Environmental Dechlorination of PCBs", JF Brown, Jr., et al., Env. Tox. & Chemistry, vol. 6, pp. 579–593, Jan. 1987.
"Reductive Dehalogenations of Halobenzoates by Anaerobic Lake Sediment Microorganism", A. Horowitz, et al., Applied and Env. Microbiology, May 1983, pp. 1459–1465.
"Rapid Assay for Screening and Characterizing Micoroorganisms for the Ability to Degrade Polychlorinated Biphenyls", DL Bedard, et al., Applied and Environmental Microbiology, Apr. 1986, p. 761–768.
U.S. Pat. Application, Ser. No. 08/376,485, filed Jan. 20, 1995, Allowed Jun. 27, 1995.

*Primary Examiner*—Peter A. Hruskoci
*Assistant Examiner*—Theodore M. Green
*Attorney, Agent, or Firm*—James Magee, Jr.

[57] ABSTRACT

A method for stimulating microbial dechlorination of the unflanked para-chlorine substituent of PCBs having one or two unflanked para-chlorine substituents in an active PCB-contaminated sediment having a population of microorganisms capable of para-dechlorinating PCBs involves incubation of the sediment with a fluorochlorobiphenyl compound such as 2,6-difluoro-4-chlorobiphenyl that has a para-chlorine at position 4, hydrogens on positions 3 and 5, and fluorines on positions 2 and 6, for a time and under conditions sufficient to decrease the levels of PCBs containing unflanked para-chlorines.

7 Claims, 6 Drawing Sheets

STIMULATION OF MICROBIAL PARA-DECHLORINATION OF POLYCHLORINATED BIPHENYLS

TECHNICAL FIELD OF THE INVENTION

This invention relates to the stimulation of microbial dechlorination of polychlorinated biphenyls having para-chlorines with no adjacent substituents.

BACKGROUND OF THE INVENTION

Polychlorinated biphenyls (PCBs) are a group of synthetic compounds formerly used for almost half a century in a wide variety of products, including hydraulic fluids, plasticizers, adhesives, fire retardants, wax extenders, dedusting agents, pesticide extenders, inks, lubricants and cutting oils. Their high chemical and thermal stability at first contributed to their commercial usefulness as industrial chemicals, but later, after possible toxicity was demonstrated, to their persistence in the environment and potential health effects. The compounds are hydrophobic and have accumulated primarily in soils and sediments where they bind with organic matter.

Polychlorinated biphenyls are composed of biphenyl molecules containing from 1 to 10 chlorines. The vast majority of PCBs in the environment are derived from once commercial mixtures that contain numerous isomers and homologs generally referred to as congeners. The positions at which chlorine may be attached to the biphenyl nucleus are shown below:

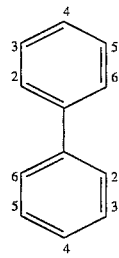

Detoxification of PCBs begins with dechlorination, which involves the stepwise removal of chlorines from the biphenyl nucleus wherein chlorine atoms are replaced with hydrogen atoms. Biological dechlorination of PCBs in contaminated sites is now well documented, and has been observed in some environments (Brown, J. F., et al., Env. Tox. Chem. 6:579–593 (1987), and Brown, J. F., et al., Science 236: 709–712 (1987). However, most naturally occurring microbially mediated dechlorination processes exhibit limited specificity and are generally restricted to removal of para- or meta-chlorines located adjacent to other chlorines, hence residual meta- and/or para-chlorines remain.

To increase dechlorination, stimulation of microbial dechlorination using various compounds such as brominated, or iodinated biphenyls and/or iodo- or bromobenzoic acids has been suggested (U.S. Pat. No. 5,227,069, and U.S. Pat. No. 5,484,729. Though beneficial in speeding up biological dechlorination, the dechlorination processes stimulated are typically limited to removal of meta- or para-chlorines located adjacent to other chlorines, and the like, particularly removal of meta-chlorines. Extensive and desirable removal of all meta- and para-chlorines does not occur, and the end-products contain 3-, 25-, and 235-chlorophenyl groups or 4-, 24-, and 246-chlorophenyl groups.

It would be beneficial to stimulate the microbial dechlorination of PCB congeners that have residual meta or para-chlorines, particularly to stimulate microbial para-dechlorination in concert with other types of microbial dechlorination involving other positions on the biphenyl ring, and "lonely para" dechlorination, i.e., para-dechlorination of rings that have no meta-chlorines.

SUMMARY OF THE INVENTION

It is an object of the invention to provide a method for stimulating microbial dechlorination of PCB congeners having para-chlorines without adjacent substituents. Such para-chlorines are referred to as unflanked or lonely para-chlorines.

It is another object of the invention to provide a method for stimulating microbial dechlorination of PCB congeners having para-chlorines that can be used in concert with other methods that dechlorinate other PCB congeners.

These and other objects are achieved by the present invention, which provides a method for accelerating microbial dechlorination of unflanked para-chlorines on PCBs in aqueous sediment which contains indigenous microorganisms capable of dechlorinating PCBs having unflanked para-chlorines by first identifying sediment containing the microorganisms that exhibit the desired activity, and then incubating this "active" sediment with a chlorinated biphenyl compound having on one phenyl ring a para-chlorine at position 4, hydrogens on positions 3 and 5, and fluorines at positions 2 and 6, hereinafter referred to as fluorochlorobiphenyls for a time and under conditions sufficient to achieve removal of about 20% or more of the unflanked para-chlorines. Specific examples of suitable compounds for such para-dechlorination include 2,6-difluoro-4-chlorobiphenyl, 2,6,2'-trifluoro-4-chlorobiphenyl, 2,6,2'-trifluoro-4,4'-dichlorobiphenyl, 2,6,2',6'-tetrafluoro-4,4'-dichlorobiphenyl, and mixtures thereof. A particularly preferred compound is 2,6-difluoro-4-chlorobiphenyl.

In the practice of the invention, sediment is screened for the presence of indigenous microorganisms capable of dechlorinating PCBs having unflanked para-chlorines by measuring the amount of PCBs having unflanked para-chlorines in the sediment; adding to a portion of the sediment containing these PCBs a chlorinated biphenyl compound having on one phenyl ring a para-chlorine at position 4, hydrogens on positions 3 and 5, and fluorines on positions 2 and 6; allowing the resulting admixture to incubate at a temperature between about 8' and about 30° C., preferably between about 12' and 25° C., for a period of about 90 days; and measuring the amount of PCBs having unflanked para-chlorines in the sediment after incubation. Active sediment is identified by observation that the amount of PCBs having unflanked para-chlorines has decreased, preferably by at least about 10%, and most preferably by at least 20%, in comparison with sediment incubated under the same conditions in the absence of the fluorochlorobiphenyl. The fluorochlorobiphenyls listed above, namely 2,6-difluoro-4-chlorobiphenyl, 2,6,2'-trifluoro-4-chlorobiphenyl, 2,6,2'-trifluoro-4,4'-dichlorobiphenyl, 2,6,2',6'-tetrafluoro-4,4'-dichlorobiphenyl are particularly preferred in one embodiment. The concentration of the compounds in the screening step typically varies between about 350 micromolar and 5 millimolar.

The first indication that the sediment contains a population of microorganisms that can be stimulated to remove unflanked para chlorines from PCBs will be the dechlorination of the added fluorochlorobiphenyl to fluorobiphenyl. The second indication will be formation of PCB congeners that are formed by para dechlorination of the target PCBs. The dechlorination stimulated by the fluorochlorobiphenyl targets primarily the unflanked para chlorines on 4-, 24-, and 246-chlorophenyl rings. Removal of para chlorines from other chlorophenyl rings is generally less effective and is better stimulated by certain brominated biphenyls as described in our previous patent (U.S. Pat. No. 5,227,069). Therefore, the effectiveness of dechlorination stimulated by fluorochlorobiphenyl in any particular sediment will primarily depend on the proportion of PCB congeners having 4-, 24-, and 246-chlorophenyl rings and can be measured in terms of the decreases in those congeners and the corresponding increases in the daughter products.

DETAILED DESCRIPTION OF THE INVENTION

Figure 1:
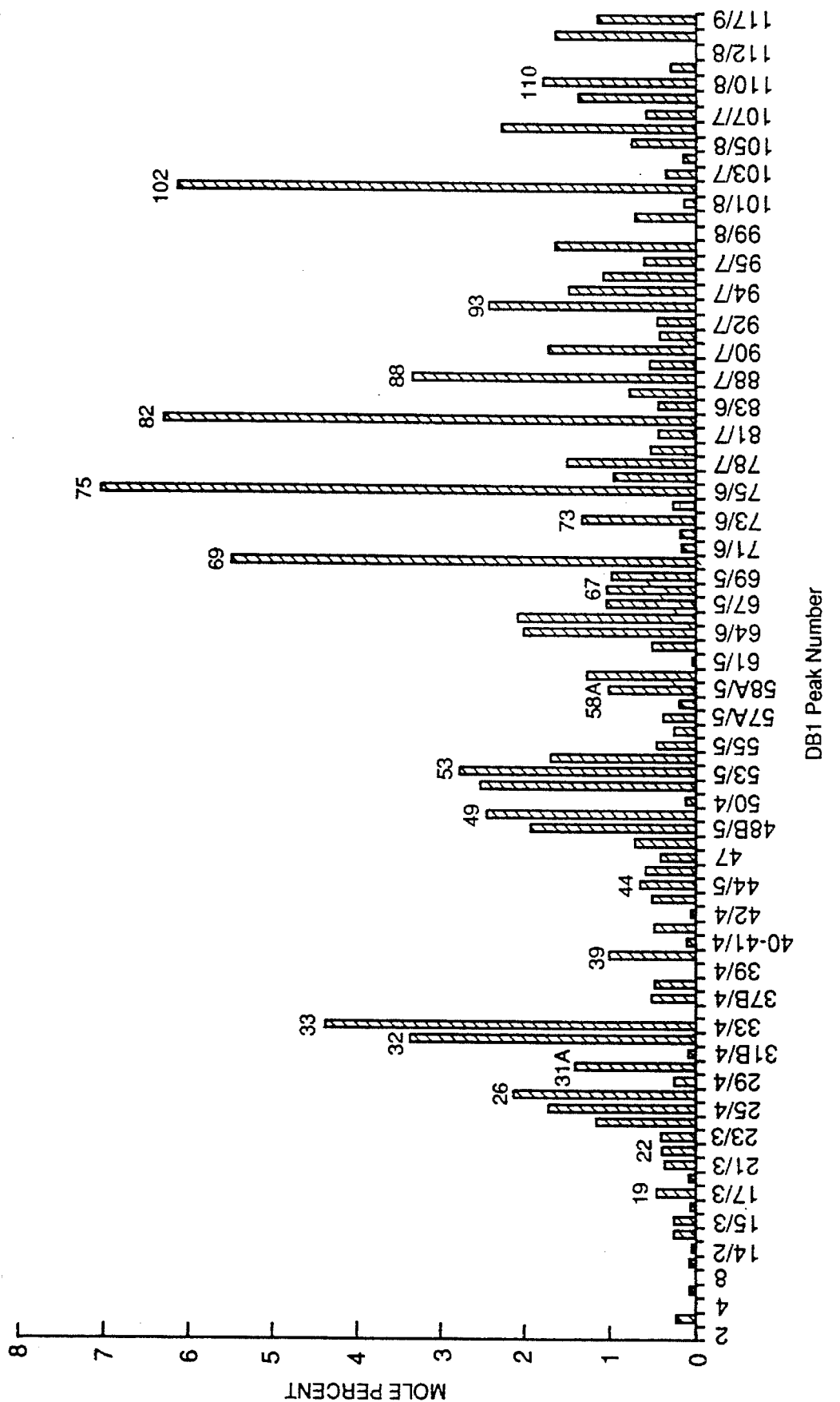
FIG. 1 is a bar graph showing the congener distribution of PCBs in an illustrative sediment sample as determined by capillary gas chromatography.

This invention is based upon the finding that certain fluorochlorobiphenyl compounds bearing at least one chlorine in the para-position and having fluorines in both ortho-positions of the same phenyl ring can be used to stimulate microbial dechlorination of unflanked para-chlorines in aqueous sediment contaminated with PCBs having para-chlorines. The compounds can be used to stimulate unflanked para-dechlorination in combination with other methods that stimulate microbial dechlorination.

By "polychlorinated biphenyls" or "polychlorinated biphenyl compounds" is meant any chlorinated biphenyl compound and mixtures thereof, such as, for example, industrial chemical products comprising mixtures of numerous congeners marketed under names Aroclor, Clophen, Fenclor, Kanechlor, Phenoclor, Pyralene and Santotherm. Notwithstanding the "poly" prefix, the term specifically includes compounds bearing a single chlorine substituent.

In the practice of the method of the invention, microbial dechlorination of unflanked para-chlorines in PCBs in aqueous sediment which contains microorganisms capable of dechlorinating PCBs having unflanked para-chlorines, herein referred to as "active sediment" is stimulated by adding to and admixing with active sediment, a fluorochlorobiphenyl having on one phenyl ring a para-chlorine at position 4, hydrogens on positions 3 and 5, and fluorine substituents at positions 2 and 6, and incubating the sediment under conditions sufficient to effect dechlorination of the unflanked para-chlorines.

Concentrations of the compounds useful in the method vary, depending upon the activity of the sediment, the concentration and identity of PCBs bearing unflanked para-chlorines to be biodegraded, and incubation conditions. Incubation conditions typically include sediment temperatures in the 8° C. to about 30° C. range and most often about 12° to about 25° C. and for times of at least 90 days and up to 6 months. The pH during incubation is generally in the 6 to 7.5 range.

Screening for active sediment containing organisms capable of dechlorinating PCBs having unflanked para-chlorines is accomplished by obtaining a sediment sample that contains PCBs having congeners bearing unflanked para-chlorines, measuring the concentration of these in the sample, adding to the sample a fluorochlorobiphenyl having on one phenyl ring a para-chlorine at position 4, hydrogens on positions 3 and 5, and fluorine substituents at positions 2 and 6 such as the ones described above, allowing the resulting admixture to incubate at a temperature between about 8° and about 30° C. for a period of about 90 days, measuring the amount of PCBs having unflanked para-chlorines in the sediment after incubation, and comparing the amount of PCBs having unflanked para-chlorines in sediment so incubated with the amount of PCBs having unflanked para-chlorines in sediment incubated under the same conditions in the absence of the fluorochlorobiphenyl. Active sediment is identified by observation that the amount of PCBs having unflanked para-chlorines incubated in the presence of the fluorochlorobiphenyl is less than that observed after incubation in its absence. A differential of between 10 to 20 percent generally indicates the presence of a suitable microorganism population.

It is an advantage of the invention that the fluorochlorobiphenyl compounds useful in the screening step can be the same as those used in the para-dechlorination step.

In the screening step, typical concentrations of fluorochlorobiphenyl compounds range from about 100 micromolar to about 5 millimolar, more narrowly from about 350 to about 2 millimolar. Ambient temperatures in the range of 12° C. to 25° C. are employed. Broadly, the pH of the sediment slurry during anoxic incubation can range from about 5 to about 8 and preferably from about 6 to about 7.5.

Some sediment that does not show activity in the screening step can be made active by the addition of a microbial inoculum that shows activity. Sediment identified as active in the screening step described above can be used as a microbial inoculum.

Accordingly, an embodiment of the invention includes a process in which a PCB-containing sediment is treated both with a fluorochlorobiphenyl such as 2,6-difluoro-4-chlorobiphenyl and an inoculum consisting of sediment containing active microorganisms with the desired dechlorinating activity. Such an inoculum is prepared by prior treatment of an appropriate sediment with the fluorochlorobiphenyl. A 1% inoculum is usually sufficient.

This is useful even if the sediment to be treated contains the appropriate microorganisms because adding an active inoculum will accelerate dechlorination by decreasing the lag period that occurs before dechlorination begins. The inoculum can be prepared from the sediment that is to be treated by incubating the sediment with the fluorochlorobiphenyl in the laboratory until the desired dechlorination activity begins as evidenced by dechlorination of the fluorochlorobiphenyl and by decreases in PCB congeners containing 4-, 24-, and 246-chlorophenyl rings and increases in the corresponding products of para dechlorination.

If the sediment to be treated does not contain the appropriate microorganisms, addition of an active inoculum prepared from a sediment that does contain the appropriate microorganisms in addition to the fluorochlorobiphenyl may enable use of our method.

The method of this invention is useful in removing para-chlorines from PCB rings bearing no meta-substituents. As discussed above, PCB congeners with unflanked para chlorines are extremely stable and have heretofore been difficult to remove by previously described microbially mediated dechlorination methods.

The method of the invention is particularly useful in combination with previously described biodegradation methods that typically involve meta-dechlorination. The method of the invention, for example, can be used following enhanced meta-dechlorination stimulated by brominated or iodinated biphenyls or by iodo- and bromobenzoic acids described above. Dechlorination of products of these meta biodechlorinations is achieved with the method of the invention so that a more complete dechlorination of an array of PCB congeners is achieved.

The practice of the method of the invention appears to stimulate the activity of microorganisms present in the sediment by providing a substrate similar to that which is to be biodegraded. Thus, it is another advantage of the invention that this bioremediation enhancement can be achieved without identification of specific microorganisms per se in active sediment. All that is required is a screening step that can be employed in a consistent manner to determine the presence of appropriate microbial activity. Therefore, the method is applicable to bioremediation enhancement on a large scale and in different locations, even though the locations might possibly contain different microorganisms to be incubated under different conditions.

Dechlorination is achieved using the method of the invention in sediment under water or in PCB-contaminated soil or landfill sites that can be submerged in water.

As used herein, the term "effective amount" when used with respect to the remediation of contaminated sediment means an amount or concentration of the fluorochlorobiphenyl compound in the sediment which substantially enhances the rate or degree of dechlorination of the PCB congeners having unflanked para-chlorines. In general, fluorochlorobiphenyl concentrations of at least about 700 micromolar are effective for remediation of contaminated sediment sites. A preferred range of concentrations for fluorochlorobiphenyl compounds is from about 700 to about 2100 micromolar.

The effective concentrations can be estimated by reference to the screening step results.

In the process of the invention, all or a portion of a site can be selected for remediation. A substantially uniform dispersion of the fluorochlorobiphenyl in the sediment is desirable. The following examples are presented to further illustrate and explain the present invention.

EXAMPLES

The PCB congener distribution from a sample of PCB-contaminated pond sediment, shows some evidence of meta-dechlorination (FIG. 1). For simplicity we will use a designation that specifies the chlorines on each ring separately. For example, 2,2'4,4'-tetrachlorobiphenyl will be referred to as 24-24-CB. The presence of GC peaks 14/15(4-4-CB, and 25-2-CB), and (24-2-CB), 17(26-4-CB), 19(26-26-CB), 23/24(25-4-CB, 24-4-CB), 25(25-26-CB), 26(24-26-CB) 29(23-26-CB), 31A(25-25-CB), 32(24-25-CB), 33(24-24-CB), 37A(246-26-CB), 37B(23-25-CB), 39(25-35-CB), 40/41(24-35-CB, 236-26-CB), and 42(23-23-CB) provide evidence of this natural dechlorination.

Slurries of the sediment were prepared with double distilled water (30 ml and 60 ml total slurry volume, 2 parts wet sediment: 3 parts water) inside an anaerobic chamber to minimize oxygen concentrations in the slurries. The slurries were amended with 2,6-difluoro-4-chlorobiphenyl in methanol to a final concentration of 350 μM. The experiments were set up in triplicate with controls sterilized by autoclaving. Aliquots of the slurries for PCB analysis were sampled every 3 weeks. The PCBs were extracted by vigorous shaking (24 hours) with anhydrous ether (5 volumes) and acid-treated copper (to remove elemental sulfur). PCB samples were initially analyzed by gas chromatography (GC) with an electron capture detector (ECD) and DB-1 capillary column (J&W Scientific; 30 m by 0.25 mm I.D. and 0.25 μM film thickness) to visually detect unflanked para-dechlorination activity. When unflanked para-dechlorinating activity became evident, PCB samples were analyzed by a GC equipped with a mass spectrometer (MS) detector and a DB-1 column to quantify the extent of dechlorination.

Figure 2:
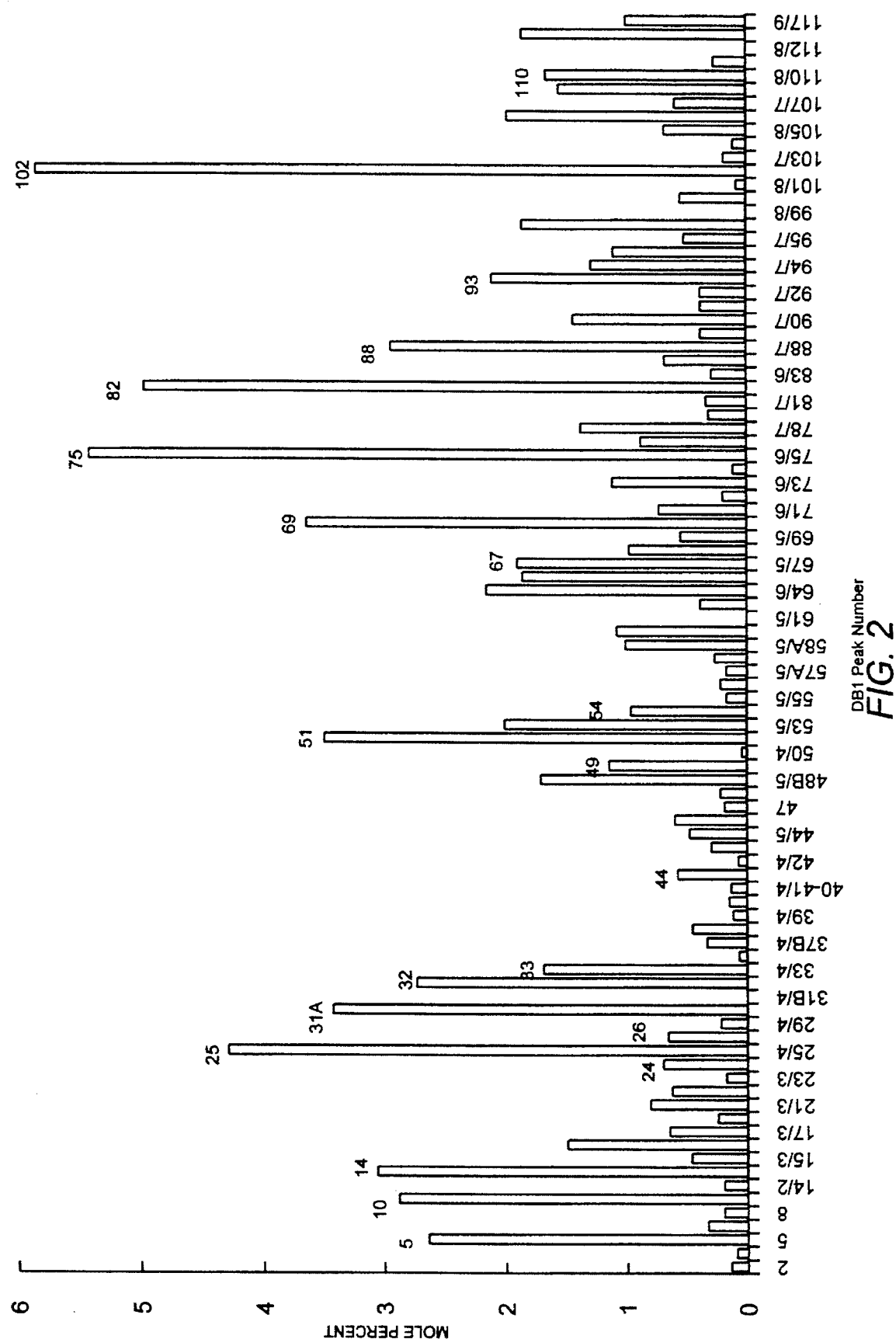
FIG. 2 is a bar graph showing the congener distribution of PCBs from the same sediment after incubation with 2,6-difluoro-4-chlorobiphenyl. The PCBs exhibit congener specific unflanked para-dechlorination as determined by gas chromatography

Autoclaved controls showed no change throughout the experiment. Unflanked para-dechlorination activity in the sediment PCB slurries was first detected at 34 days. Although the live slurries did not all become active at the same time, 16 sets of triplicates were active by day 94. Active slurries were visually identified by the decreases in peaks 15(24-2-CB), 26(24-26-CB), 32(24-25-CB), 33(24-24-CB), and 48A(24-34-CB) and by corresponding increases in peaks 5(2-2-CB), 10(26-2-CB), 14(25-2-CB), and 25(25-26-CB)(FIG. 2). The active PCB-dechlorinating sediment slurries described here were subsequently used as inocula for slurries that had previously been meta dechlorinated by the addition of 2,6-dibromobiphenyl in earlier experiments.

Figure 3:
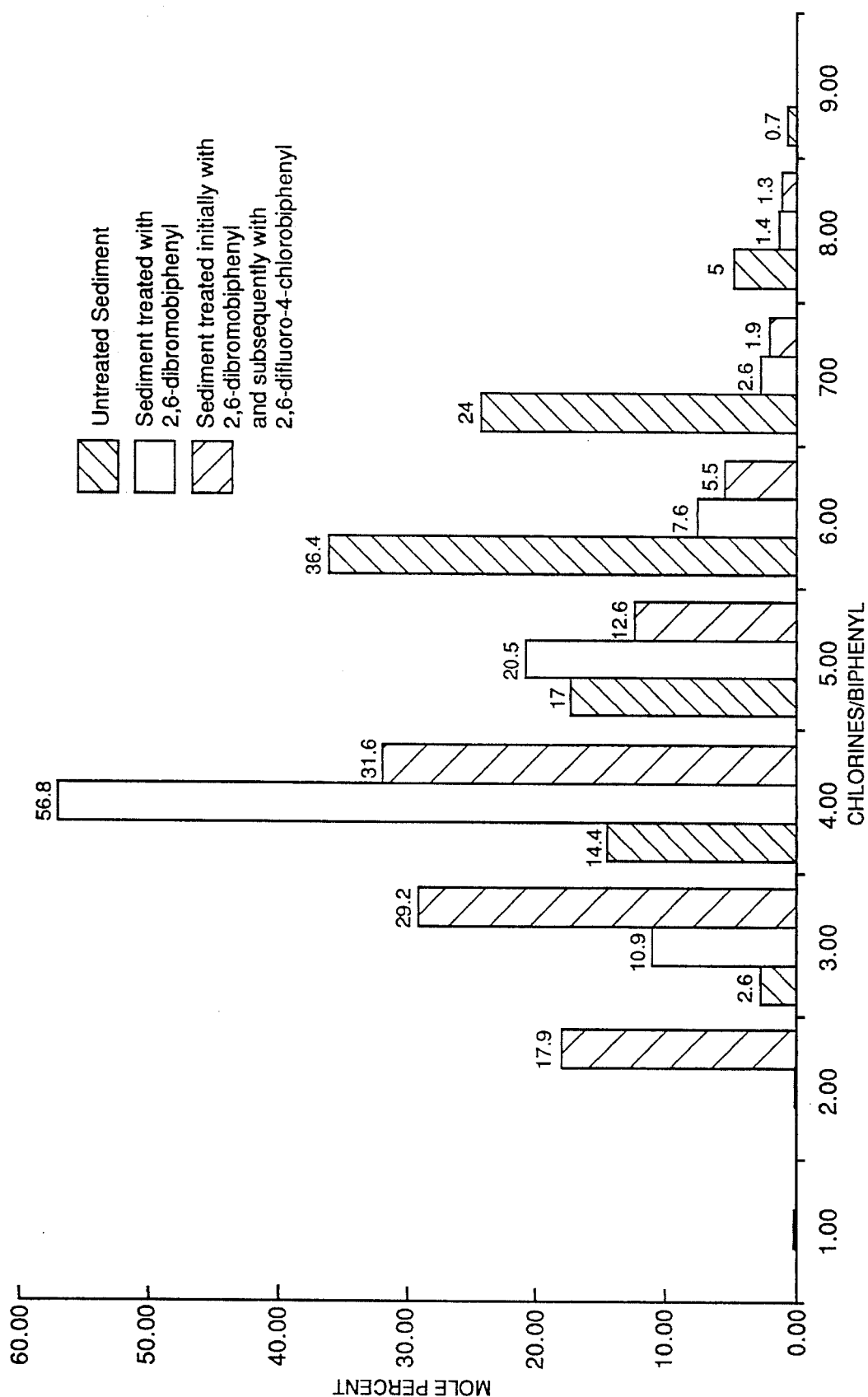
FIG. 3 is a bar graph showing the homolog distribution of the sediment PCBs after sequential treatment with 2,6-dibromobiphenyl and 2,6-difluoro-4-chlorobiphenyl.
Figure 4:
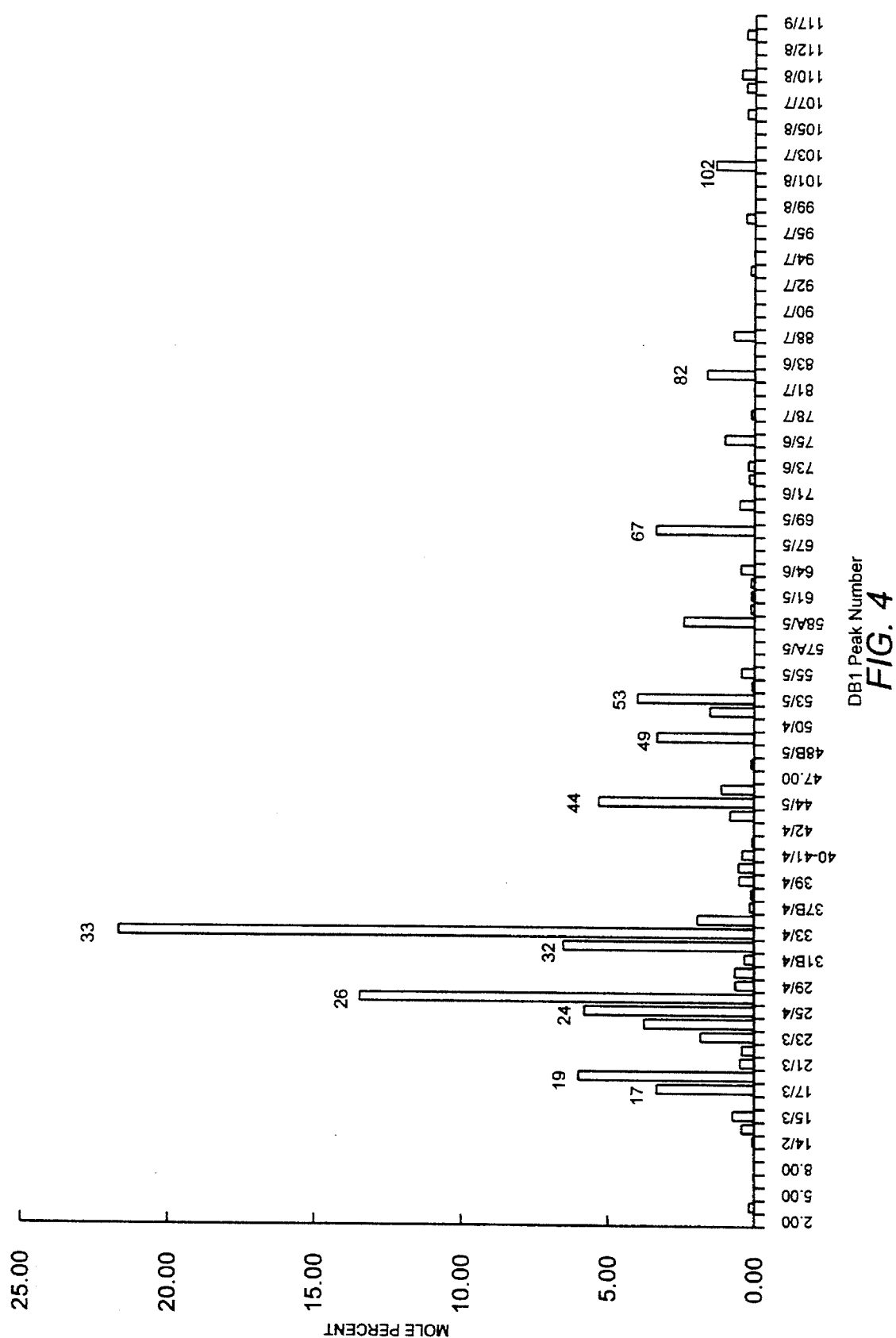
FIG. 4 is a bar graph showing the congener distribution of sediment PCBs after treatment with 2,6-dibromobiphenyl which stimulated the removal of primarily meta- chlorines.
Figure 5:
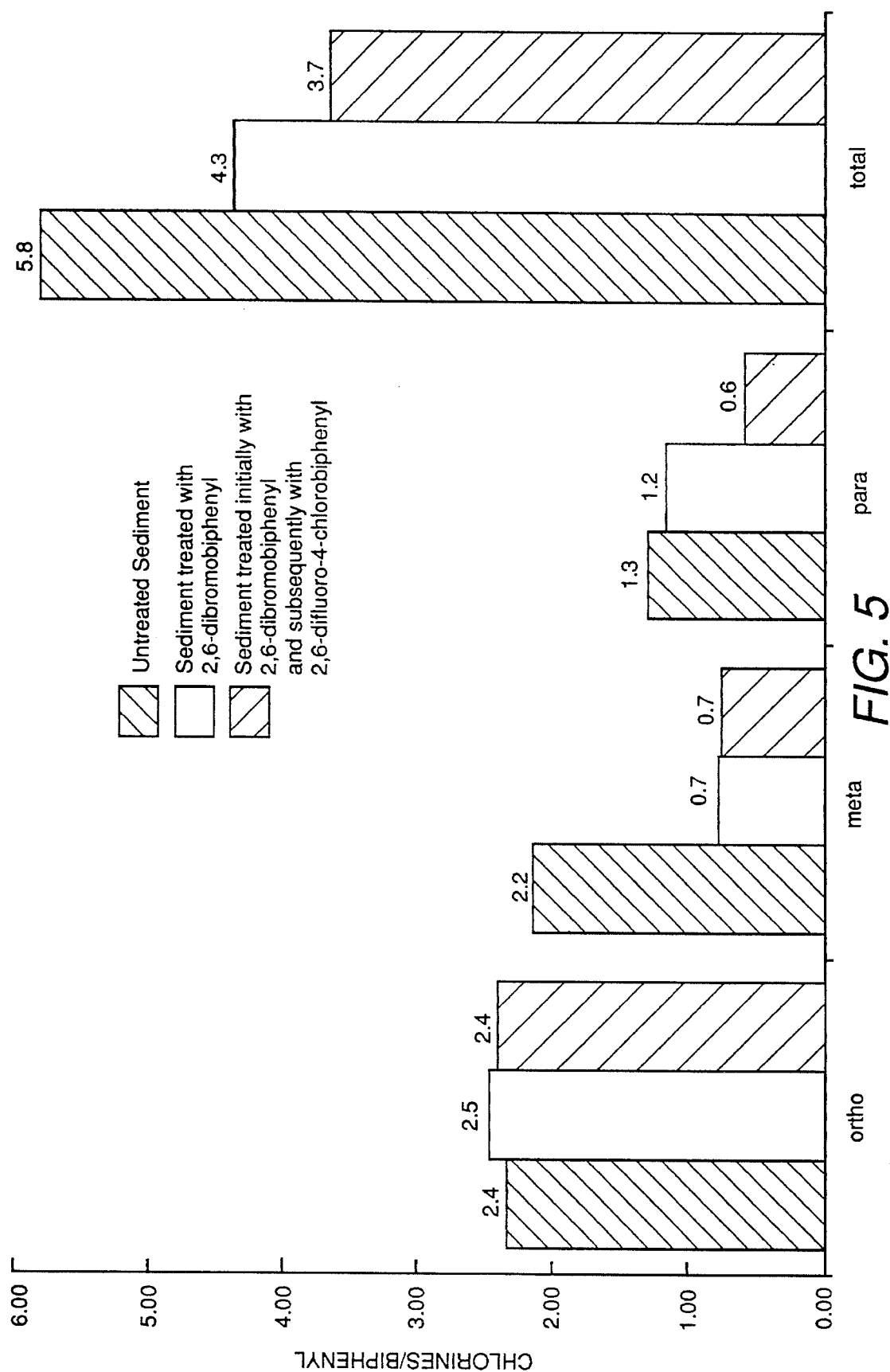
FIG. 5 is a bar graph showing ortho-, meta-, para-, and total chlorine distribution for the sediment PCBs from FIG. 1 after sequential treatment with 2,6-dibromobiphenyl and 2,6-difluoro-4-chlorobiphenyl.

Most of the PCBs in the sediment (66.1 mole percent) contain 6 to 9 chlorines per biphenyl (FIG. 3). In contrast, for sediment PCBs that have been microbially dechlorinated using 2,6-dibromobiphenyl, but without the fluorochlorobiphenyl compounds of this invention the proportion of PCBs containing 6 to 9 chlorines was only 11.6 mole percent, and the proportion containing 3 to 4 chlorines was increased from 17 to 67.7 mole percent (FIGS. 3 and 4). This type of dechlorination is due almost exclusively to the loss of meta-chlorines that are adjacent to an ortho- or a para-chlorine. Hence, 234-, 245- and 2345- chlorophenyl rings are dechlorinated to 24-chlorophenyl groups and 34-, 236- and 2346-chlorophenyl rings are dechlorinated to 4-, 26- and 246-chlorophenyl rings, respectively. There was a 68% decrease in meta-chlorines and an overall decrease of 25% of the total chlorines (FIG. 5). In the untreated sample sediment (FIG. 1) only 13 mole percent of the PCBs contained an unflanked para-chlorine, i.e. a 24-, 246-, or a 4-chlorophenyl group. But after the extensive meta-dechlorination stimulated by 2,6-bromobiphenyl (FIG. 4), 65 percent of the PCB congeners contained an unflanked para-chlorine.

Sediment samples containing PCBs that were previously meta-dechlorinated in the presence of 2,6-dibromobiphenyl were slurried (30 ml total slurry volume) as described above. All slurries were amended with 2,6-difluoro-4-chlorobiphenyl in methanol to a final concentration of 700 μM. In addition to the 2,6-difluoro-4-chlorobiphenyl, some slurries were inoculated with sediment slurries containing active unflanked para-dechlorinating microorganisms. In the anaerobic chamber, the meta-dechlorinated sediment slurries were vortexed for 60 seconds to mix and suspend the sediments in the water. A 1% aliquot (0.3 ml) was removed and discarded. A slurry inoculum (1%, 0.3 ml) from the screened sediment PCB slurries showing unflanked para-dechlorinating activity was added. Aliquots for PCB analysis were removed weekly. Analysis was performed as described above.

Figure 6:
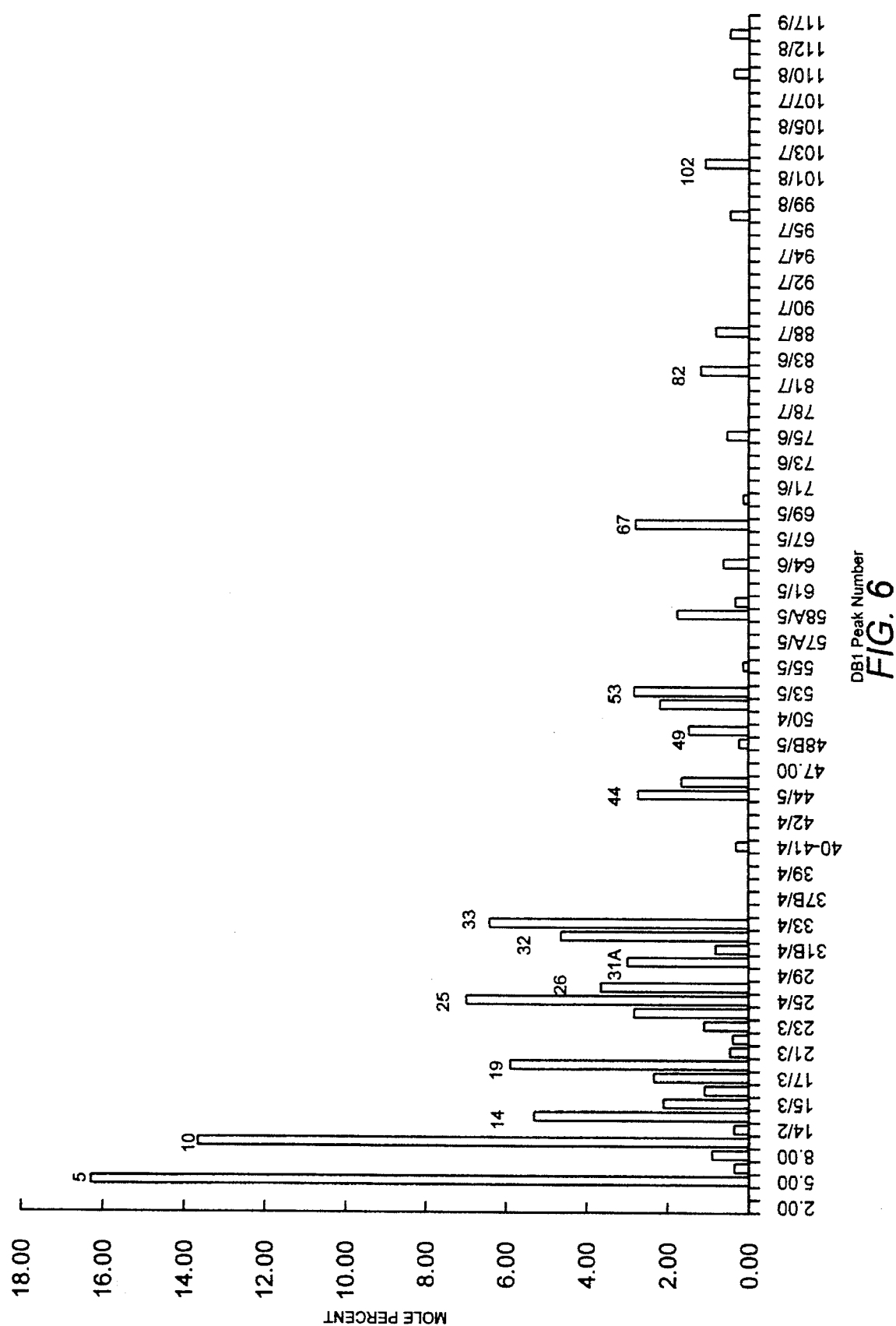
FIG. 6 is a bar graph showing the congener distribution of sediment PCBs after sequential treatment with 2,6-dibromobiphenyl and 2,6-difluoro-4-chlorobiphenyl.

Substantial unflanked para-dechlorination activity was seen in all of the slurries 66 days after the addition of the 2,6-difluoro-4-chlorobiphenyl whether or not an inoculum from an actively dechlorinating slurry was used. Slurries that were inoculated began to exhibit unflanked para-dechlorination activity within 14 days of amendment, whereas the slurries without an inoculum did not exhibit activity until after 28 days. By 66 days, all slurries had reached the same extent of dechlorination (FIG. 6). Visually, there were large decreases in peaks 49(236-24-CB), 33(24-24-CB), 32(24-25-CB), 26(24-26-CB) and 24(24-4-CB) and large increases in peaks 5(2-2-CB), 10(26-2-CB) and 14(25-2-CB). As a result of the addition of the 2,6-difluoro-4-chlorobiphenyl, there was a 44% reduction of the tetrachlorobiphenyls to 31.6 mole percent and a corresponding increase in the di- and trichlorobiphenyls from 10.9 to 47.1 mole percent (FIG. 3). This loss was due almost exclusively to the loss of para-chlorines which decreased by 50%, resulting in an overall decrease of 36% in total chlorines per biphenyl (FIG. 5). The impact of 2,6-difluoro-4-chlorobiphenyl was greatest when added to PCBs that were previously meta-dechlorinated. GC/MS detection showed a decrease of 35 mole percent in congeners containing unflanked para-chlorines and a combined increase of 28 mole percent for peaks 2(2CB), 5(2-2-CB) and 10(2 6-2-CB). The latter PCB congeners are degradable by aerobic bacteria.

The projected pathway for unflanked para-dechlorination of the available substrates is as follows:

| | | | | | | | | |
|---|---|---|---|---|---|---|---|---|
| 2-4 | → | 2- | (?) | | | | | |
| (8) | | (2) | | | 24-24 | → | 24-2 | → | 2-2 |
| 4-4 | → | (?) | | | (33) | | (15) | | (5) |
| (14) | | | | | 23-24 | → | 23-2 | | |
| 24-2 | → | 2-2 | | | (38) | | (17) | | |
| (15) | | (5) | | | 246-25 | → | 25-26 | | |
| 24-3 | → | 2-3 | | | (43) | | (25) | | |
| (22) | | (7) | | | 246-24 | → | 24-26 | → | 26-2 |
| 24-4 | → | 2-4 | → | 2- (?) | (44) | | (26) | | (10) |
| (24) | | (8) | | (2) | 236-24 | → | 236-2 | | |
| 24-26 | → | 26-2 | | | (49) | | (27) | | |
| (26) | | (10) | | | 2356-24 | → | 2356-2 | | |
| 24-25 | → | 25-2 | | | (67) | | (48B) | | |
| (32) | | (14) | | | | | | | |

Note: numbers in parenthesis refer to GC peak numbers.

Using the same techniques and measurements, unflanked para-dechlorination was also stimulated by 2,6-difluoro-4-chlorobiphenyl in PCB-contaminated lake sediment from a different site.

What is claimed is:

1. A method for accelerating microbial dechlorination of unflanked para-chlorines in PCBs in aqueous sediment which contains microorganisms capable of dechlorinating PCBs having such para-chlorines, which comprises the steps of (1) screening the sediment for presence of microorganisms capable of dechlorinating PCBs having unflanked para-chlorines by
   (a) adding to a portion of the sediment containing PCBs a fluorochlorobiphenyl compound having on one phenyl ring a para-chlorine at position 4, hydrogen at positions 3 and 5, and fluorine substituents at positions 2 and 6;
   (b) allowing the resulting admixture to incubate at a temperature between about 8° and about 30° C. for a period of about 90 days;
   (c) measuring the amount of PCBs having unflanked para-chlorines in the sediment after incubation;
   (d) comparing the amount of PCBs having unflanked para-chlorines in sediment so incubated with the amount of PCBs having unflanked para-chlorines in sediment incubated under the same conditions in the absence of the fluorochlorobiphenyl compound; and
   (e) identifying the sediment as active by observation that the amount of PCBs having unflanked para-chlorines incubated in the presence of the fluorochlorobiphenyl compound is less than that observed by incubation in its absence; and (2) adding to and admixing with the active sediment an effective amount of a fluorochlorobiphenyl compound having on one phenyl ring a para-chlorine at position 4, hydrogens at positions 3 and 5, and fluorine substituents at positions 2 and 6, and incubating the sediment under conditions sufficient to effect dechlorination of the unflanked para-chlorines.

2. A method according to claim 1 wherein the compound used in the screening step and in the dechlorination step is 2,6-difluoro-4-chlorobiphenyl.

3. A method according to claim 1 wherein the concentration of the compound used in the screening step ranges from about 100 micromolar to 5 millimolar.

4. A method according to claim 1 which employs a nutrient in the dechlorination step 5. A method for microbial dechlorination of unflanked para-chlorine substituents of PCBs having one or two unflanked para-chlorine substituents in an active PCB-contaminated sediment having a population of microorganisms capable of para-dechlorinating PCBs, provided by inoculating the sediment with an active inoculum in the presence of 2,6,-difluoro-4-chlorobiphenyl identified by incubating the sediment with 2,6,-difluoro-4-chlorobiphenyl for about 90 days at about 8° to 30° C. and observing that the levels of PCBs having unflanked para-chlorines has decreased as compared to a corresponding sediment incubated in the absence of 2,6-difluoro-4-chlorobiphenyl and incubating the sediment under conditions and for a sufficient time whereby dechlorination proceeds so that the level of unflanked para-chlorines decreases by at least about 20% of the initial level in the sediment.

6. A method according to claim 5 wherein the concentration of 2,6-difluoro-4-chlorobiphenyl in the screening step is between about 100 micromolar and 5 millimolar.

7. A method for accelerating microbial dechlorination of unflanked para-chlorines from PCBs in aqueous sediment which comprises incubating the sediment in the presence of an inoculum containing microorganisms capable of removing unflanked para-chlorines from polychlorinated biphenyl congeners and in the presence of a fluorochlorobiphenyl compound having on one phenyl ring a para-chlorine at position 4, hydrogen at positions 3 and 5, and fluorine substitutents at positions 2 and 6.

* * * * *